United States Patent [19]

Jensen

[11] Patent Number: 4,518,388

[45] Date of Patent: May 21, 1985

[54] OSTOMY POUCH WITH REDUCED FRICTION INSERT

[75] Inventor: Ole R. Jensen, River Vale, N.J.

[73] Assignee: E. R. Squibb & Sons, Princeton, N.J.

[21] Appl. No.: 388,177

[22] Filed: Jun. 14, 1982

[51] Int. Cl.³ .............................................. A61F 5/44
[52] U.S. Cl. .................................................. 604/332
[58] Field of Search .............. 604/277, 328, 332–345, 604/347, 348, 355, 394, 397; 128/760, 767

[56] References Cited

U.S. PATENT DOCUMENTS

| | | | |
|---|---|---|---|
| 3,302,647 | 2/1967 | Marsan | 128/283 |
| 3,351,061 | 11/1967 | Nolan | 128/283 |
| 3,352,737 | 11/1967 | Jordan | 156/514 |
| 3,618,606 | 11/1971 | Brown | 128/283 |
| 3,804,091 | 4/1974 | Nolan et al. | 604/333 |
| 3,805,789 | 4/1974 | Marsan | 604/336 |
| 3,906,951 | 9/1975 | Ling | 604/336 |
| 4,411,659 | 10/1983 | Jensen et al. | 604/332 |

OTHER PUBLICATIONS

"A Premium for our Premium", Hollister Incorporated, Libertyville, Illinois, 60048.

*Primary Examiner*—Stephen C. Pellegrino
*Assistant Examiner*—J. L. Kruter
*Attorney, Agent, or Firm*—James & Franklin

[57] ABSTRACT

An insert, having a non-heat sealable surface, is affixed to a first thin film wall. The first wall is aligned with a second thin film wall, with the non-heat sealable surface of the insert facing the interior surface of the second wall. The walls are welded along their periphery to form the contour of the pouch. An adhesive-backed label is then welded to the exterior of the second wall. The insert prevents the interior surfaces of the walls from being sealed together as the adhesive-backed label is welded, simplifying the manufacturing process. The non-heat sealable surface of the insert may be composed of a low friction material to facilitate movement of solid waste within the pouch.

7 Claims, 4 Drawing Figures

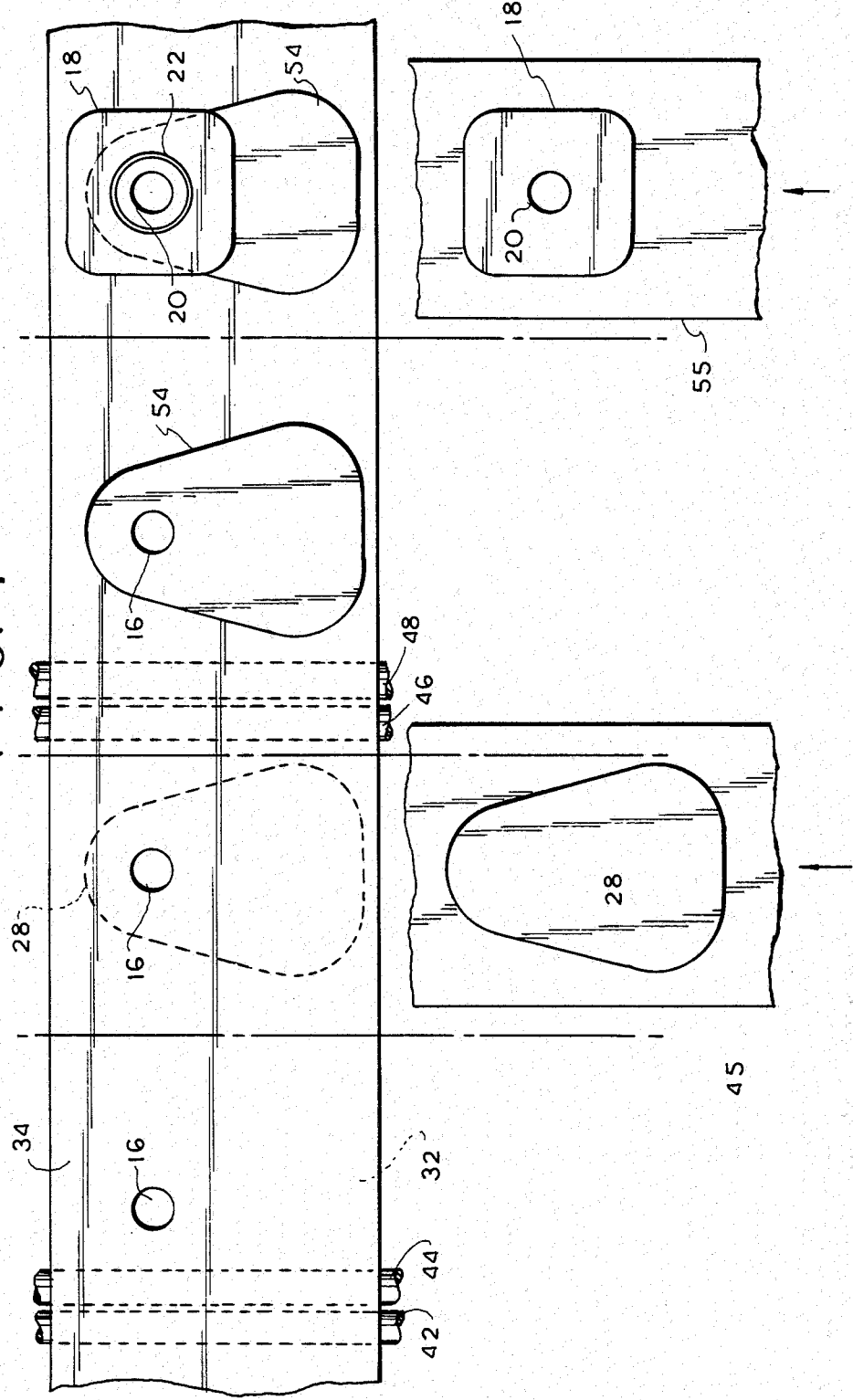

OSTOMY POUCH WITH REDUCED FRICTION INSERT

The present invention relates to ostomy pouches and, more particularly, to an ostomy pouch having an insert and to a simplified method and apparatus for manufacturing same.

Subsequent to ileostomy, colostomy, and similar surgical procedures, it is often necessary for the patient to utilize an ostomy pouch to cover the stoma and to collect material as it is discharged. Over the years, ostomy pouches of a variety of different sizes, shapes, and constructions have been utilized. Various materials and adhesives have been developed to increase the utility and wearability of the pouches.

The basic pouch comprises first and second thin film walls which are sealed, by heat welding or the like, along their periphery to form the contour of the pouch. One wall has an aperture therein designed to align with the stoma. Affixed to the exterior surface of the aperture bearing wall is an adhesive-backed flange or label designed to secure the pouch to the skin surrounding the stoma. The adhesive-backed label has an aperture which aligns with the aperture in the pouch wall.

The adhesive-backed label may be affixed to the exterior surface of the pouch wall in any suitable manner, such as by welding, if the label and pouch wall are composed of the same material, or by lamination, if different materials are employed. For the purposes of this specification, the term "weld" will be used to refer to either process, depending upon the materials used.

In one method of manufacturing such an ostomy pouch, the adhesive-backed label is first welded to one pouch wall. Thereafter, the other pouch wall is sealed to the pouch wall bearing the adhesive-backed label, such as by welding or the like, to form the contour of the pouch.

This manufacturing method is possible only if the adhesive-backed label does not extend, at any point, beyond the periphery of the pouch and, particularly, the weld which forms the contour. If the adhesive-backed label extends beyond the contour of the pouch, the adhesive-backed label will cover a portion of the contour, shielding same from the welding tool, thereby preventing the pouch walls from being completely sealed. The weld cannot be performed from the underside of the pouch (opposite to the side to which the label is affixed) because the presence of the label prevents the formation of a continuous seal at the points on the pouch aligned with the edges of the label.

It is, however, desirable to employ a relatively large adhesive-backed label such that the pouch can be affixed to the skin over a large area, thereby insuring that the pouch will remain secured to the body and will support the weight of the pouch and the contents thereof. Because of the manufacturing difficulty related to the use of an adhesive-backed label which is larger than the contour of the pouch, the contour of the top portion of the pouch, which is aligned with the label has, in the past, often been enlarged to accommodate an adhesive-backed label of increased dimension. Aside from adding to the cost of the pouch because of the extra pouch wall material required, enlarging the top portion of the pouch often had the undesirable result of causing the outer wall to pull away from the inner wall as the pouch filled with material.

In my co-pending U.S. application Ser. No. 286,495, filed July 24, 1981, and entitled "A Method of Manufacturing Ostomy Pouches," which issued on June 14, 1983 into U.S. Pat. No. 4,388,135, I describe a method for manufacturing an ostomy pouch with an adhesive-backed label which extends beyond the contour of the pouch. In that method, the two pouch walls are first partially contour-welded together, over an area extending from the top edge of the pouch, past the region where the weld used to affix the adhesive-backed label to the pouch wall will be situated. A separator member is temporarily introduced between the partially sealed pouch walls. The adhesive-backed label is then affixed to the pouch wall by the ring weld surrounding the aperture. The separator member is then withdrawn from the partially formed pouch and the remainder of the contour of the pouch is sealed by another welding operation.

The separator member serves to prevent the pouch wall to which the adhesive label is affixed from being welded to the other pouch wall during welding of the adhesive-backed label. If the separator member was not present, the walls would be welded together as the adhesive-backed label is affixed, resulting in an unusable structure.

While the above-described manufacturing method permits the use of an enlarged adhesive-backed label, without requiring that the dimensions of the pouch itself be increased, it has the disadvantage of requiring an additional manufacturing operation. In particular, the method requires that the contour welding operation occur twice—once to weld a first portion of the contour prior to affixing the adhesive-backed label, and once to complete the contour weld subsequent to the application of the adhesive-backed label. Consequently, this manufacturing method is more time consuming and more costly than the standard manufacturing method.

Ostomy pouches of conventional design are known to suffer from additional drawbacks. Since ostomy pouches are often worn in public, it is desirable that this be done as discretely as possible. It is therefore necessary to reduce the noise level of the pouch film material to prevent embarrassment of the patient.

Another drawback of conventional ostomy pouches relates to the movement of material and particularly solid waste within the pouch. Conventional pouch wall material may tend to impede the movement of solid waste within the pouch because of friction developed between the wall surface and the material. This friction may prevent the contents of the pouch from sliding to the bottom of the pouch.

It is, therefore, a prime object of the present invention to provide an ostomy pouch with an insert and a method for manufacturing same.

It is another object of the present invention to provide an ostomy pouch with an insert and method of manufacturing same wherein the adhesive-backed label extends beyond the contour of the pouch and wherein only a single contour welding operation is required.

It is another object of the present invention to provide an ostomy pouch with an insert and a method for manufacturing same wherein the welding operation which affixes the adhesive-backed label to the pouch takes place after the contour of the pouch has been completely welded.

It is another object of the present invention to provide an ostomy pouch with an insert and a method for manufacturing same wherein the pouch walls are separated so as not to be joined together as the adhesive-backed label is welded to the pouch.

It is another object of the present invention to provide an ostomy pouch with an insert and a method of manufacturing same wherein the noise level of the pouch wall material is reduced.

It is another object of the present invention to provide an ostomy pouch with an insert and a method of manufacturing same wherein movement of the pouch contents within the interior of the pouch is facilitated.

In accordance with the first aspect of the present invention, an ostomy pouch is provided including first and second pouch walls sealed along their contour. The one pouch wall has an aperture therein. An adhesive-backed label, also having an aperture, is affixed to that pouch wall, with the aperture therein aligned with the aperture in that wall. An insert is situated within the pouch between the interior surfaces of the pouch walls.

The insert is provided with a non-heat sealable surface which faces the interior surface of the aperture bearing wall. As used herein, the term "non-heat sealable" refers to any substance which will not seal, bond or weld to the wall material when subjected to normal welding conditions. The insert may be composed wholly of non-heat sealable material, or may be composed of a base which has a non-heat sealable coating or surface layer.

The label is affixed to the aperture bearing pouch wall within a given area. The insert is aligned with the given area. In this manner, the pouch walls are separated and cannot be sealed together by the welding operation employed to affix the adhesive-backed label to the aperture bearing wall.

Means are provided for affixing the insert to the interior surface of the other pouch wall. Preferably, the insert is substantially co-extensive with the pouch wall to which it is affixed.

The non-heat sealable surface of the insert is preferably formed of a material which also has a low coefficient of friction. Such a material will serve to reduce the friction between the surface of the insert and the solid waste material and, thus, facilitate the movement of solid waste material within the pouch. For example, silicone is suitable for this purpose because it is both non-heat sealable and has a low coefficient of friction. If a silicone layer is provided, because it is a non-heat sealable substance, the base material of the insert may be composed of material which would normally be heat sealable, such as polyethylene. This structure will prevent the insert from bonding or welding to the pouch wall, as well as providing the non-stick function.

The adhesive-backed label preferably extends beyond the contours of the pouch. In this manner, the pouch may be secured to the patient over a larger area to enhance security and comfort.

In accordance with another aspect of the present invention, a method of manufacturing ostomy pouches is provided. The method includes the steps of placing an insert between first and second pouch walls. The first and second pouch walls are then sealed along a continuous line to form the contour of the pouch, with the insert situated between the pouch walls. An adhesive-backed label is thereafter welded to the exterior of the second pouch wall.

The adhesive-backed label is welded to the second pouch wall within a given area. The method further comprises the step of placing the insert in a position aligned with the given area.

The method preferably further comprises the step of affixing the insert to the interior surface of the first pouch wall. This step may be performed by providing a layer of adhesive or the like between the insert and the interior surface of the first pouch wall or, if the insert is composed of a base of heat sealable material with a non-heat sealable surface layer, by welding.

The step of sealing the first and second pouch walls along a continuous line preferably comprises the step of welding the pouch walls along the continuous line. The method also preferably comprises the step of forming an aperture in the second pouch wall.

In accordance with another aspect of the present invention, an apparatus for manufacturing ostomy pouches is provided. The apparatus includes means for affixing an insert to a first pouch wall and means for sealing the first and second pouch walls along a continuous line to form the contour of the pouch, with the insert situated in the interior of the pouch. Means are also provided for welding an adhesive-backed label to the exterior surface of the second pouch wall.

The affixing means may comprise a means for providing an adhesive layer between the insert and the interior surface of the first pouch wall. However, if an insert with a heat sealable base is used, the affixing means may comprise a welding tool.

The means for sealing the first and second pouch walls along a continuous line preferably comprises a welding means. In addition, means for forming an aperture in the second pouch wall may be provided.

To the accomplishment of the above and to such other objects which may hereinafter appear, the present invention relates to an ostomy pouch having an insert and a method for manufacturing same, as described in the following specification and recited in the annexed claims, taken together with the accompanying drawings, wherein like numerals refer to like parts, and in which:

Figure 1:
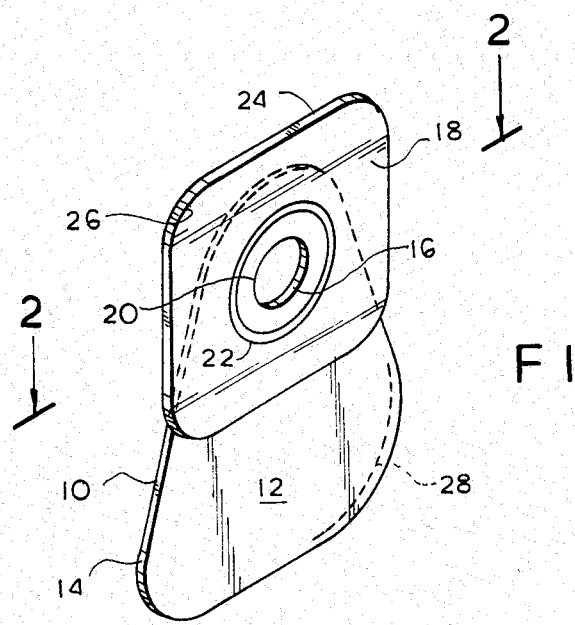
FIG. 1 is an isometric view of the ostomy pouch with internal insert of the present invention.
Figure 2:
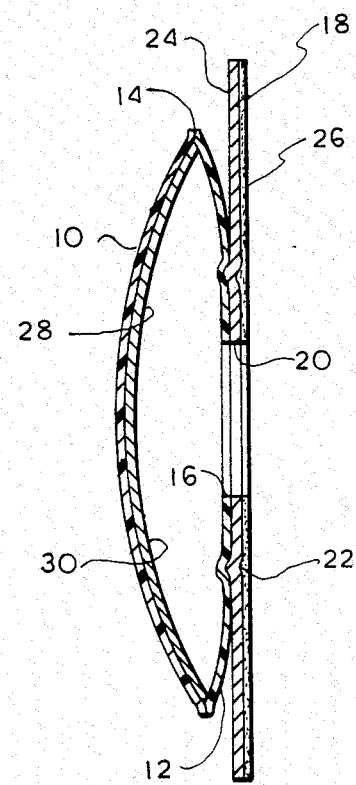
FIG. 2 is a cross-sectional view of the ostomy pouch with internal insert of the present invention, taken along line 2—2 of FIG. 1.

FIGS. 1 and 2 depict a typical ostomy pouch with insert in accordance with the present invention. The pouch comprises a first or outer wall 10 and a second or inner wall 12, each composed of thin, moisture impermeable, odorproof, thermo-plastic film or laminate. The interior surfaces of walls 10 and 12 are heat sealed along the periphery 14 thereof, so as to form the contour of the pouch. Wall 12 is provided with a stoma-surrounding aperture 16. An adhesive-backed label 18 is affixed to the exterior surface of wall 12 with the aperture 20 therein aligned with aperture 16. Adhesive-backed label 18 is affixed to wall 12 by means of a ring weld 22, which surrounds, but is spaced from, the aligned apertures 16 and 20.

While only a single ring weld 22 for bonding label 18 to wall 12 is shown in the drawing, it should be understood that multiple ring welds, for example, three spaced concentric welds, may be preferred instead of the single weld 22 in certain cases. The materials selected for pouch wall 12 and layer 24 will dictate the configuration of the weld. However, for purposes of simplicity, only a single weld is illustrated and discussed herein.

The purpose of adhesive-backed label 18 is to affix the pouch to the skin of the wearer. The adhesive-backed label 18 must serve to securely retain the pouch to the skin for an extended period of time. For this reason, it is preferable to have a relatively large adhesive-backed label—larger than the contour of the pouch—such that a relatively large area of skin surrounding the stoma can be gripped by the adhesive. To permit the skin beneath the adhesive-backed label to breathe, it is preferable to have the adhesive layer be microporous. In addition, the adhesive-backed label should be as flexible as possible to insure comfort.

Adhesive-backed label 18 comprises a porous base 24 coated with an adhesive layer 26. The porous base 24 can be formed of woven or non-woven fabric such as a Rayon web, an open mesh polymeric substance such as an open mesh polyethylene or polypropylene or a polymeric foam such as polyurethane foam, polyethylene foam, etc., or a non-woven material made from polyester fibers, polypropylene fibers, nylon fibers, composite olefin fibers or cellulose fibers which are commercially available. For example, the spun-laced polyester product Sontara 8003, manufactured by DuPont, has proved excellent for this purpose.

The adhesive layer 26 is preferably formed of a homogeneous blend of one or more pressure-sensitive viscous or elastomeric materials having intermittently dispersed therein one or more water soluble hydrocolloid gums and may also include one or more thermoplastic elastomers and/or one or more swellable cohesive strengthening agents.

Situated along the interior surface of wall 10 is a thin flexible insert 28. Insert 28 has one surface which faces but is spaced from the interior surface of wall 12 and a second surface which is adjacent and preferably affixed to the interior surface of wall 10. The composition of insert 28 depends upon the manner in which label 18 is affixed to wall 12. If label 18 is affixed to wall 12 by welding, the surface of insert 28 facing the interior surface of wall 12 must be formed of a non-heat sealable material. If label 18 is affixed to wall 12 by other means, such as adhesive, the surface of insert 28 facing the interior surface of wall 12 need not be composed of non-heat sealable material.

If a non-heat sealable surface is required, insert 28 may be composed entirely of non-heat sealable material, in which case it could be affixed to wall 10 by an adhesive layer. Alternatively, insert 28 may be composed of a base made of heat-sealable material, such as polyethylene, with a non-heat sealable layer 30, coated on the surface facing wall 12. In the latter case, the insert may be heat welded to the interior surface of wall 10, if desired.

Whether or not layer 30 is required to be composed of a non-heat sealable material, this layer is preferably composed of a low friction material. The low friction property facilitates movement of solid waste within the pouch such that gravity will be effective to cause the solid waste to move toward the bottom of the pouch.

Some materials, such as silicone, are both non-heat sealable and have a low coefficient of friction. Thus, the use of silicone as layer 30 provides both functions and is preferred.

The presence of insert 28 also tends to reduce the crinkling noise often associated with the pouch walls. This feature is particularly important if the pouch is to be worn in public in a discrete manner.

Thus, insert 28 provides multiple functions. If label 18 is to be welded to wall 12, it prevents wall 10 and 12 from being joined during the welding process. Surface layer 30, if composed of low friction material, facilitates the movement of solid waste within the pouch. Moreover, the insert tends to reduce the noise associated with conventional pouch structures.

As shown in the drawings, insert 28 is substantially co-extensive with the interior surface of wall 10. (Actually, insert 28 is slightly smaller than wall 10 to permit the interior edge of wall 10 to be welded to the interior edge of wall 12 to form the pouch contour.) This is the preferable configuration because it insures a reduction of friction between the waste material and the entire interior of wall 10, as well as contributing most effectively to the reduction of noise. However, to meet the process requirements when a weld is used to affix label 18 to wall 12, namely, to prevent the weld from also joining wall 10 to wall 12, it is necessary that insert 28 have a non-heat sealable surface, only slightly larger than the ring weld and be positioned on wall 10 in alignment with the location on wall 12 in which the ring weld will be situated. Thus, the position and size of the ring weld used to join adhesive-backed label 18 to wall 12 determines the location and minimum size of insert 28.

Figure 3:
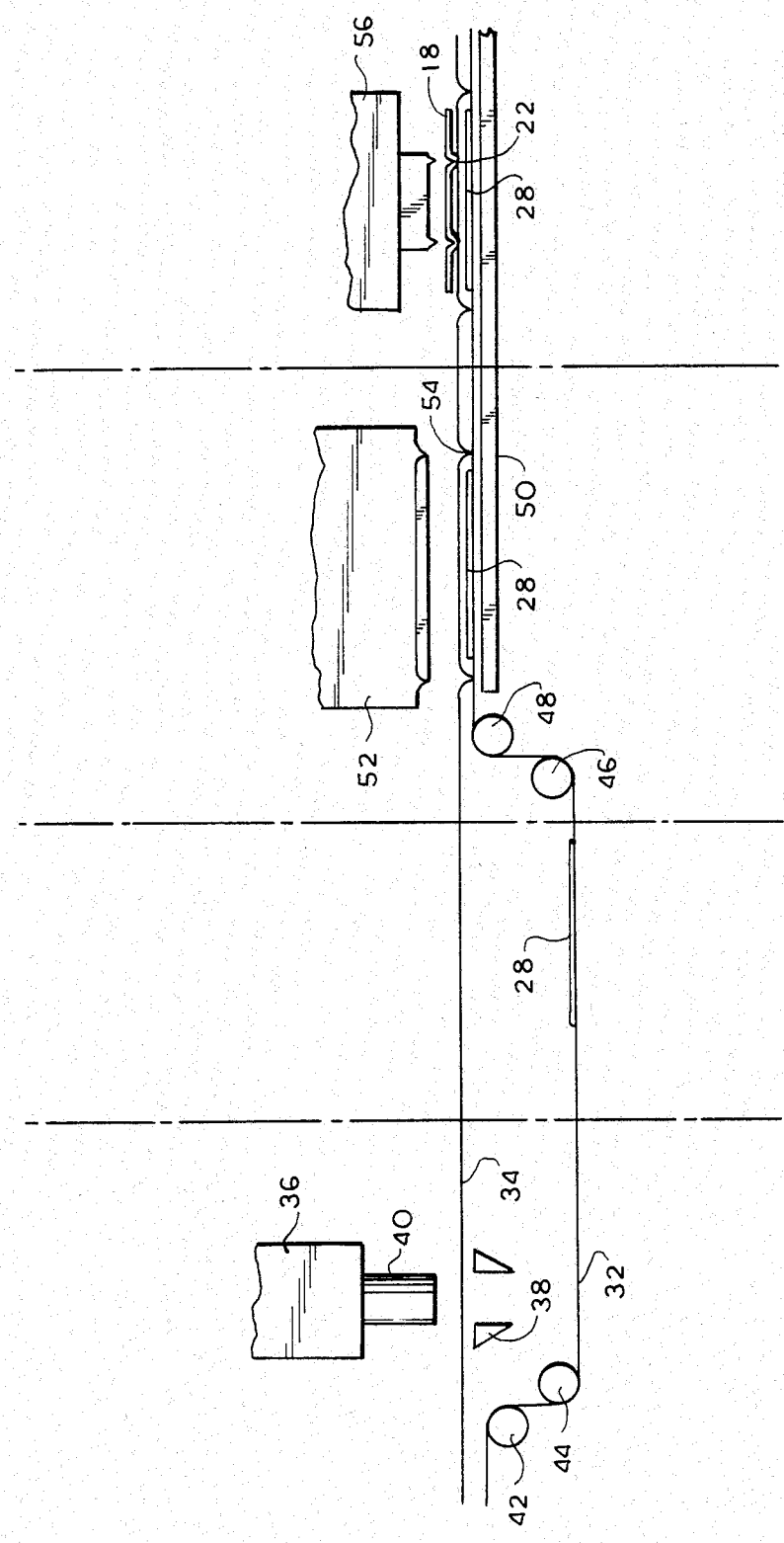
FIG. 3 is a side view of a schematic representation showing the method and apparatus for manufacturing the ostomy pouch of the present invention; and, FIG. 4 is a top view of a schematic representation of the method and apparatus for manufacturing the ostomy pouch of the present invention.

The preferred process for manufacturing an ostomy pouch of the type depicted in FIGS. 1 and 2 employs a weld operation to affix label 18 to wall 12, as explained below with reference to FIGS. 3 and 4. FIGS. 3 and 4, respectively, show side and top views of the four stations of the manufacturing process and schematically represent the equipment necessary to perform the various fabrication operations. In these figures, the various stations in the fabrication process are represented in sequence from left to right, such that the first station in the process is depicted on the lefthand portion of each Figure, and the last station in the process is depicted on the righthand portion of each Figure.

Two superimposed webs 32, 34 of weldable plastic sheet material, which eventually will form walls 10 and 12, respectively, of the pouch, are moved step-wise through the four separate process stations. At the first station, web 34 passes between a punch 36 and a support 38. Punch 36 has a cylindrical tool 40, the dimensions of which match closely the dimensions of the circular opening in support 38. Punch 36 is reciprocated towards support 38 so as to form the stoma surrounding aperture 16 in web 34. Guide rollers 42, 44 are provided to separate web 32 from web 34 during the punching operation.

The vertically separated webs 32 and 34 are then transferred to the second processing station wherein the insert 28 is affixed to the upper surface of web 32. At this station, an insert feed conveyor 45, moving in a direction substantially perpendicular to the direction of movement of webs 32 and 34, provides a supply of inserts 28. Each insert, in turn, is removed from conveyor 45 and is affixed to the upper surface of web 32. This may be accomplished through the use of an adhesive layer and the insert can be affixed to the web either manually or automatically. If the insert has a base made of heat sealable material, the insert may be affixed by welding. Inserts 28 are fabricated to have the same or somewhat smaller size and the same general shape as the wall 10 of the pouch will eventually have. At the end of the second station, web 32 travels around another pair of guide rollers 46, 48 and is brought back to a position immediately beneath web 34.

At the next station, the webs pass over a base or support 50 and below a contour welding electrode 52 which is moved downwardly toward base 50 so as to weld the respective interiors of webs 32 and 34 together along a continuous line which will form the contour of the pouch. The contour weld is shown as numeral 54. Once the pouch walls have been sealed along their contour, with insert 28 situated on the interior surface of the outer wall, the formed pouch is transferred to the final station in the fabrication process.

At the final station in the fabrication process, the adhesive-backed label 18 is affixed to the pouch. A label feed conveyor 55 moving in a direction perpendicular to the direction of movement of the webs, brings adhesive-backed label 18 to the station. The label 18 is removed from the feed conveyor and placed on top of web 34 such that the aperture 20 in the label 18 is in registration with the aperture 16 previously punched in web 34. A second welding electrode 56 is then moved toward support 50 so as to provide the ring weld 22 around the registered apertures, but spaced a small distance therefrom. Because insert 28 has a non-heat sealable surface, it will not bond with the interior surface of wall 12 during the ring welding operation and will prevent walls 10 and 12 from being welded together as the label is affixed. The completed pouch is then transferred to an accumulating and packing station (not shown) where the pouches are packaged and made ready for shipment.

It should now be readily appreciated that, from a process standpoint, non-heat sealable insert 28 is required when label 18 is welded to wall 12 in order to prevent the ring weld 22 from also joining wall 10 of the pouch to wall 12. In order to fulfill this function, insert 28 must be aligned with, and at least as large as, the area in which the ring weld 22 will be situated. Thus, the position and dimensions of ring weld 22 define the position and minimum dimensions of the insert. However, as indicated above, it is preferable to have insert 28 cover the entire interior surface of wall 10 of the pouch in order to reduce noise and facilitate movement of solid waste along the entire interior of wall 10.

The process of the present invention, unlike prior art processes for fabricating ostomy pouches, permits the use of an adhesive-backed label which extends beyond the contour of the pouch, but requires only a single contour welding operation to seal the pouch walls. Accordingly, the process of the present invention is simplified, as compared with previously known fabrication processes, because of the elimination of certain operations required by the prior art process, such as the dual partial contour welding steps and the necessity for the insertion and subsequent withdrawal of a temporary separation member to permit the welding of the adhesive label to the pouch wall. Consequently, the cost of fabrication is reduced and, at the same time, a structurally and functionally superior product is achieved.

While only a single embodiment of the present invention has been disclosed herein for purposes of illustration, it is obvious that many variations and modifications could be made thereto. It is intended to cover all of these variations and modifications which fall within the scope of the present invention, as defined by the following claims:

I claim:

1. An ostomy pouch comprising first and second pouch walls sealed along their contour, said first pouch walls having an aperture therein, an adhesive-backed label having an aperture, said label being heat-seal affixed to said one pouch wall, with said aperture therein aligned with said aperture in said one pouch wall, and an insert comprising non-heat-sealable material, said insert being situated within said pouch between the interior surfaces of said pouch walls substantially completely and permanently and affixed to the interior surface of said second pouch walls in registration with the affixation of said label to said one pouch wall.

2. The pouch of claim 1, wherein said insert comprises a base with a non-heat sealable surface layer facing said one pouch wall.

3. The pouch of either claims 1 or 2, wherein said insert is substantially co-extensive with said other wall.

4. The pouch of either of claims 1 or 2, wherein the surface of said insert facing said one pouch wall is coated with a material having a low coefficient of friction.

5. The pouch of either of claims 1 or 2, wherein said label extends beyond the contour of said pouch.

6. The pouch of either of claims 1 or 2, wherein said insert comprises a polyethylene base with a silicone surface coating.

7. The pouch of claim 1, wherein said insert is of a material to reduce friction between the surface of the insert and the collected waste material in the pouch.

* * * * *